US012569553B2

(12) United States Patent
Campbell et al.

(10) Patent No.: US 12,569,553 B2
(45) Date of Patent: Mar. 10, 2026

(54) SHINGLES VACCINES COMPRISING A TLR9 AGONIST

(71) Applicant: Dynavax Technologies Corporation, Emeryville, CA (US)

(72) Inventors: John D. Campbell, San Francisco, CA (US); Randall N. Hyer, Gwynedd Valley, PA (US); Robert S. Janssen, Palm Springs, CA (US); David Novack, Oakland, CA (US)

(73) Assignee: Dynavax Technologies Corporation, Emeryville, CA (US)

( * ) Notice: Subject to any disclaimer, the term of this patent is extended or adjusted under 35 U.S.C. 154(b) by 648 days.

(21) Appl. No.: 17/910,334

(22) PCT Filed: Mar. 9, 2021

(86) PCT No.: PCT/US2021/021544

§ 371 (c)(1),
(2) Date: Sep. 8, 2022

(87) PCT Pub. No.: WO2021/183540

PCT Pub. Date: Sep. 16, 2021

(65) Prior Publication Data

US 2023/0061403 A1      Mar. 2, 2023

Related U.S. Application Data

(60) Provisional application No. 62/987,243, filed on Mar. 9, 2020.

(51) Int. Cl.
*A61K 39/25* (2006.01)
*A61P 31/22* (2006.01)
*A61K 39/00* (2006.01)

(52) U.S. Cl.
CPC .............. *A61K 39/25* (2013.01); *A61P 31/22* (2018.01); *A61K 2039/545* (2013.01); *A61K 2039/55505* (2013.01); *A61K 2039/55561* (2013.01)

(58) Field of Classification Search
None
See application file for complete search history.

(56) References Cited

U.S. PATENT DOCUMENTS

| | | | |
|---|---|---|---|
| 4,769,239 | A | 9/1988 | Ellis et al. |
| 5,653,976 | A | 8/1997 | Shiraki et al. |
| 5,824,319 | A | 10/1998 | Vafai |
| 5,997,880 | A | 12/1999 | Calandra et al. |
| 6,180,369 | B1 | 1/2001 | Vafai |
| 6,589,940 | B1 | 7/2003 | Raz et al. |
| 7,357,936 | B1 | 4/2008 | Garcon |
| 7,763,450 | B2 | 7/2010 | Robinson et al. |
| 7,939,084 | B1 | 5/2011 | Hanon et al. |
| 7,951,384 | B2 | 5/2011 | Morrison et al. |
| 8,080,255 | B2 | 12/2011 | Smith et al. |
| 8,506,967 | B2 | 8/2013 | Smith et al. |
| 8,551,756 | B2 | 10/2013 | Smith et al. |
| 8,592,197 | B2 | 11/2013 | Robinson et al. |
| 8,697,088 | B2 | 4/2014 | Smith et al. |
| 8,846,051 | B2 | 9/2014 | Kew et al. |
| 8,951,537 | B2 | 2/2015 | Smith et al. |
| 8,974,797 | B2 | 3/2015 | Morrison |
| 8,992,939 | B2 | 3/2015 | Smith et al. |
| 9,050,290 | B2 | 6/2015 | Smith et al. |
| 9,144,607 | B2 | 9/2015 | Robinson et al. |
| 9,180,180 | B2 | 11/2015 | Smith et al. |
| 9,216,212 | B2 | 12/2015 | Morrison |
| 9,243,041 | B2 | 1/2016 | Weiner et al. |
| 9,381,239 | B2 | 7/2016 | Smith et al. |
| 9,399,059 | B2 | 7/2016 | Morrison |
| 9,464,276 | B2 | 10/2016 | Smith et al. |
| 9,474,799 | B2 | 10/2016 | Robinson et al. |
| 9,623,104 | B2 | 4/2017 | Smith et al. |
| 9,636,410 | B2 | 5/2017 | Brito et al. |
| 9,694,066 | B2 | 7/2017 | Smith et al. |
| 9,937,253 | B2 | 4/2018 | Smith et al. |
| 9,951,317 | B2 | 4/2018 | Smith et al. |
| 9,956,280 | B2 | 5/2018 | Robinson et al. |
| 9,994,619 | B2 | 6/2018 | Weiner et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,183,074 | B2 | 1/2019 | Brito et al. |

(Continued)

FOREIGN PATENT DOCUMENTS

| | | |
|---|---|---|
| CN | 102517302 A | 6/2012 |
| CN | 104407147 A | 3/2015 |

(Continued)

OTHER PUBLICATIONS

Dooling et al, (Jan. 2018, p. 103-108).*
Johnson et al., (Vaccine, 2009 p. 3045-3052).*
Anonymous (Jan. 10, 2022). "Dynavax Highlights 2022 Priorities and Announces Initiation of Phase 1 Clinical Trial for its Shingles Vaccine Candidate," Dynavax, 2 pages.
Arvin, A.M. (1996). "Varicella-Zoster Virus," Clinical Microbiology Reviews 9(3):361-381.
Bender, E. (Jan. 11, 2018). "Why a New Vaccine for Preventing Shingles Received FDA Approval and a CDC Recommendation," Neurotodayonline, 3 pages.
Bharucha, T. et al. (2017). "A Critical Appraisal of Shingrix, A Novel Herpes Zoster Subunit Vaccine (HZ/Su or GSK1437173A) for Varicella Zoster Virus," Human Vaccines & Immunotherapeutics 13(8):1789-1797.
Braun, R.P. et al. (1988). "Immunogenic Duplex Nucleic Acids Are Nuclease Resistant," J. Immunol. 141(6):2084-2089.

(Continued)

*Primary Examiner* — Agnieszka Boesen

(74) *Attorney, Agent, or Firm* — MORRISON & FOERSTER LLP

(57) ABSTRACT

The present disclosure relates to immunogenic compositions comprising a varicella zoster vims (VZV) glycoprotein E antigen and a toll-like receptor 9 (TLR9) agonist, such as an oligonucleotide comprising an unmethylated cytidine-phospho-guanosine (CpG) motif. The immunogenic compositions are suitable for stimulating an immune response against VZV in an individual in need thereof.

24 Claims, 3 Drawing Sheets

Specification includes a Sequence Listing.

(56) References Cited

U.S. PATENT DOCUMENTS

| | | | |
|---|---|---|---|
| 10,188,723 B2 | 1/2019 | Smith et al. | |
| 10,238,731 B2 | 3/2019 | Ciaramella et al. | |
| 10,272,150 B2 | 4/2019 | Ciaramella et al. | |
| 10,350,289 B2 | 7/2019 | Meyer et al. | |
| 10,874,734 B2 | 12/2020 | Nam et al. | |
| 10,940,198 B2 | 3/2021 | Nam et al. | |
| 11,045,540 B2 | 6/2021 | Ciaramella | |
| 2002/0150889 A1 | 10/2002 | Eickmann et al. | |
| 2006/0121052 A1 | 6/2006 | Sotelo-Morales et al. | |
| 2008/0171079 A1 | 7/2008 | Hanon et al. | |
| 2008/0171688 A1 | 7/2008 | Sotelo-morales et al. | |
| 2009/0043280 A1 | 2/2009 | Dalton | |
| 2009/0081157 A1* | 3/2009 | Kornbluth | A61K 39/12 |
| | | | 424/85.4 |
| 2010/0119550 A1 | 5/2010 | Gomi et al. | |
| 2010/0166736 A1 | 7/2010 | Agrawal et al. | |
| 2010/0330122 A1 | 12/2010 | Smith et al. | |
| 2011/0008838 A1 | 1/2011 | Smith et al. | |
| 2011/0045059 A1 | 2/2011 | Hanon et al. | |
| 2011/0189233 A1 | 8/2011 | Nagaike et al. | |
| 2013/0101620 A1 | 4/2013 | Nagaike et al. | |
| 2013/0344100 A1 | 12/2013 | D'aoust et al. | |
| 2014/0030292 A1 | 1/2014 | Franti et al. | |
| 2014/0227309 A1 | 8/2014 | Smith et al. | |
| 2014/0227322 A1 | 8/2014 | Daoust et al. | |
| 2014/0271829 A1 | 9/2014 | Lilja et al. | |
| 2014/0356390 A1 | 12/2014 | Kew et al. | |
| 2016/0000902 A1 | 1/2016 | Smith et al. | |
| 2016/0193324 A1 | 7/2016 | Meyer et al. | |
| 2017/0035864 A1 | 2/2017 | Theriault | |
| 2017/0112914 A1 | 4/2017 | Ballou, Jr. et al. | |
| 2017/0136110 A1 | 5/2017 | Ballou, Jr. et al. | |
| 2017/0342442 A1 | 11/2017 | Lilja et al. | |
| 2017/0354727 A1 | 12/2017 | Kew et al. | |
| 2018/0008700 A1 | 1/2018 | Heineman et al. | |
| 2018/0036403 A1 | 2/2018 | Burkhart et al. | |
| 2018/0117141 A1 | 5/2018 | Park et al. | |
| 2018/0264098 A1 | 9/2018 | Kew et al. | |
| 2018/0271970 A1 | 9/2018 | Ciaramella et al. | |
| 2018/0271975 A1 | 9/2018 | Ciaramella et al. | |
| 2018/0289792 A1 | 10/2018 | Ciaramella et al. | |
| 2018/0296662 A1 | 10/2018 | Ciaramella et al. | |
| 2018/0303929 A1 | 10/2018 | Ciaramella et al. | |
| 2018/0311336 A1 | 11/2018 | Ciaramella et al. | |
| 2018/0318409 A1 | 11/2018 | Valiante et al. | |
| 2018/0360939 A1 | 12/2018 | Lemoine et al. | |
| 2018/0372745 A1 | 12/2018 | Suzuki et al. | |
| 2019/0008946 A1 | 1/2019 | Ciaramella et al. | |
| 2019/0008947 A1 | 1/2019 | Ciaramella et al. | |
| 2019/0038738 A1 | 2/2019 | Smith et al. | |
| 2019/0062713 A1 | 2/2019 | Smith et al. | |
| 2019/0091329 A1 | 3/2019 | Brito et al. | |
| 2019/0144507 A1 | 5/2019 | Franti et al. | |
| 2019/0216917 A1 | 7/2019 | Ciaramella et al. | |
| 2019/0240317 A1 | 8/2019 | Ciaramella et al. | |
| 2019/0298824 A1 | 10/2019 | Chen et al. | |
| 2019/0328868 A1 | 10/2019 | Nam et al. | |
| 2019/0365884 A1 | 12/2019 | Nam et al. | |
| 2021/0077616 A1 | 3/2021 | Nam et al. | |
| 2021/0187099 A1 | 6/2021 | Nam et al. | |
| 2025/0163105 A1 | 5/2025 | Janssen | |

FOREIGN PATENT DOCUMENTS

| | | | |
|---|---|---|---|
| CN | 105669838 A | 6/2016 |
| CN | 108727503 A | 11/2018 |
| CN | 109602901 A | 4/2019 |
| EP | 0192902 A2 | 9/1986 |
| EP | 0405867 B1 | 3/1995 |
| EP | 0504388 B1 | 9/2000 |
| EP | 1644037 A2 | 4/2006 |
| EP | 1721981 A1 | 11/2006 |
| EP | 1126876 B1 | 3/2007 |
| EP | 1797173 A2 | 6/2007 |
| EP | 0955059 B1 | 9/2007 |
| EP | 1917033 A2 | 5/2008 |
| EP | 1937301 A2 | 7/2008 |
| EP | 1961814 A1 | 8/2008 |
| EP | 1528914 B1 | 10/2008 |
| EP | 0651789 B2 | 5/2009 |
| EP | 0927760 B1 | 12/2009 |
| EP | 2175882 A1 | 4/2010 |
| EP | 2175883 A2 | 4/2010 |
| EP | 2176427 A1 | 4/2010 |
| EP | 2242510 A2 | 10/2010 |
| EP | 2343084 A1 | 7/2011 |
| EP | 2383343 A2 | 11/2011 |
| EP | 2471936 A2 | 7/2012 |
| EP | 2471937 A2 | 7/2012 |
| EP | 2471938 A2 | 7/2012 |
| EP | 2540312 A1 | 1/2013 |
| EP | 2364722 B1 | 11/2013 |
| EP | 2670443 A2 | 12/2013 |
| EP | 2768530 A1 | 8/2014 |
| EP | 1858917 B1 | 12/2014 |
| EP | 2590626 B1 | 10/2015 |
| EP | 2953642 A1 | 12/2015 |
| EP | 2591114 B1 | 6/2016 |
| EP | 2590676 B1 | 8/2016 |
| EP | 2281830 B1 | 12/2016 |
| EP | 2655613 B1 | 2/2017 |
| EP | 2590670 B1 | 8/2017 |
| EP | 3210631 A1 | 8/2017 |
| EP | 3233118 A1 | 10/2017 |
| EP | 2575876 B1 | 12/2017 |
| EP | 2808384 B1 | 12/2017 |
| EP | 3268036 A1 | 1/2018 |
| EP | 2718428 B1 | 3/2018 |
| EP | 2281831 B1 | 4/2018 |
| EP | 2301955 B1 | 4/2018 |
| EP | 3364949 A1 | 8/2018 |
| EP | 3364950 A1 | 8/2018 |
| EP | 3364980 A1 | 8/2018 |
| EP | 3364981 A1 | 8/2018 |
| EP | 3364982 A2 | 8/2018 |
| EP | 3364983 A2 | 8/2018 |
| EP | 3365007 A2 | 8/2018 |
| EP | 3365008 A1 | 8/2018 |
| EP | 3365009 A1 | 8/2018 |
| EP | 2729124 B1 | 10/2018 |
| EP | 2627351 B1 | 12/2018 |
| EP | 3456316 A1 | 3/2019 |
| EP | 3545972 A1 | 10/2019 |
| EP | 3560512 A1 | 10/2019 |
| EP | 3125930 B1 | 12/2020 |
| EP | 3382395 B1 | 4/2021 |
| EP | 3812394 A1 | 4/2021 |
| EP | 3520813 B1 | 4/2023 |
| EP | 3125929 B1 | 11/2023 |
| EP | 3389698 B1 | 6/2025 |
| JP | S61081792 A | 4/1986 |
| JP | H03232897 A | 10/1991 |
| KR | 101481362 B1 | 1/2015 |
| WO | 200043527 A1 | 7/2000 |
| WO | 2005020889 A2 | 3/2005 |
| WO | 2005085445 A1 | 9/2005 |
| WO | 2006042156 A2 | 4/2006 |
| WO | 2006094756 A2 | 9/2006 |
| WO | 2006128026 A2 | 11/2006 |
| WO | 2007019247 A2 | 2/2007 |
| WO | 2007047831 A2 | 4/2007 |
| WO | 2007060725 A1 | 5/2007 |
| WO | 2008148104 A1 | 12/2008 |
| WO | 2009012486 A1 | 1/2009 |
| WO | 2009012487 A2 | 1/2009 |
| WO | 2009012489 A1 | 1/2009 |
| WO | 2009105152 A2 | 8/2009 |
| WO | 2012051211 A2 | 4/2012 |
| WO | 2012083445 A1 | 6/2012 |
| WO | 2012106377 A2 | 8/2012 |
| WO | 2012171104 A1 | 12/2012 |
| WO | 2013006837 A1 | 1/2013 |
| WO | 2013055905 A1 | 4/2013 |

(56) References Cited

FOREIGN PATENT DOCUMENTS

| WO | 2014124423 | A1 | 8/2014 |
|----|------------|----|--------|
| WO | 2015115767 | A1 | 8/2015 |
| WO | 2015150567 | A1 | 10/2015 |
| WO | 2015150568 | A1 | 10/2015 |
| WO | 2016064063 | A1 | 4/2016 |
| WO | 2016096968 | A1 | 6/2016 |
| WO | 2016142880 | A1 | 9/2016 |
| WO | 2017070601 | A1 | 4/2017 |
| WO | 2017070613 | A1 | 4/2017 |
| WO | 2017070616 | A2 | 4/2017 |
| WO | 2017070618 | A1 | 4/2017 |
| WO | 2017070620 | A2 | 4/2017 |
| WO | 2017070622 | A1 | 4/2017 |
| WO | 2017070623 | A1 | 4/2017 |
| WO | 2017070624 | A1 | 4/2017 |
| WO | 2017070626 | A2 | 4/2017 |
| WO | 2017090744 |    | 6/2017 |
| WO | 2017102737 | A1 | 6/2017 |
| WO | 2018097642 | A1 | 5/2018 |
| WO | 2018104313 | A1 | 6/2018 |
| WO | 2018114892 | A1 | 6/2018 |
| WO | 2018124615 | A1 | 7/2018 |
| WO | 2018140733 | A1 | 8/2018 |
| WO | 2018170270 | A1 | 9/2018 |
| WO | 2018198085 | A1 | 11/2018 |
| WO | 2018206776 | A1 | 11/2018 |
| WO | 2018219521 | A1 | 12/2018 |
| WO | 2019106192 | A1 | 6/2019 |
| WO | 2019225962 | A1 | 11/2019 |
| WO | 2021/013798 | A1 | 1/2021 |
| WO | 202113798 | A1 | 1/2021 |
| WO | 2023122774 | A1 | 6/2023 |

OTHER PUBLICATIONS

Callegaro, A. et al. (2022, e-pub Oct. 18, 2021). "Association Between Immunogenicity and Reactogenicity: A Post Hoc Analysis of 2 Phase 3 Studies with the Adjuvanted Recombinant Zoster Vaccine," J. Infect. Dis. 226:1943-1948.

Campbell, J.D. (2017). "Chapter 2: Development of The CpG Adjuvant 1018: A Case Study," Methods Mol. Biol. 1494:15-27.

Chlibek, R. et al. (2013, e-pub. Jul. 31, 2013). "Safety and Immunogenicity of an AS01-Adjuvanted Varicella-Zoster Virus Subunit Candidate Vaccine Against Herpes Zoster in Adults ≥ 50 Years of Age," J. Infect. Dis. 208:1953-1961.

Coffman, R.L. et al. (2010). "Vaccine Adjuvants: Putting Innate Immunity to Work," Immunity 33(4):492-503, 21 pages.

Cunningham, A.L. et al. (2016). "Efficacy of the Herpes Zoster Subunit Vaccine in Adults 70 Years of Age or Older," N. Eng. J. Med. 375(11):1019-1032.

Dendouga, N. et al. (2012, e-pub. Feb. 10, 2012). "Cell-Mediated Immune Responses to a Varicella-Zoster Virus Glycoprotein E Vaccine Using Both a TLR Agonist and QS21 in Mice," Vaccine 30:3126-3135.

Dooling, K.L. et al. (Jan. 26, 2018). "Recommendations of the Advisory Committee on Immunization Practices for Use of Herpes Zoster Vaccines," MMWR, 67(3):103-108.

Fochesato, M. et al. (2016). "Comparative Preclinical Evaluation of AS01 Versus Other Adjuvant System in a Candidate Herpes Zoster Glycoprotein E Subunit Vaccine," Human Vaccines & Immunotherapeutics 12(8):2092-2095.

Garçon, N. et al. (2017). "From Discovery to Licensure, The Adjuvant System Story," Human Vaccines & Immunotherapeutics 13(1):19-33.

GenBank No. AQT34120.1 (Dec. 16, 2020). "Envelope Glycoprotein E [Human Alphaherpesvirus 3]," 2 pages.

GenBank No. P09259 (Jul. 1, 1989). "Varicella-Zoster Virus (Strain Dumas) (HHV-3) (Human Herpesvirus 3)," 3 pages.

Harbecke, R. et al. (2021). "Herpes Zoster Vaccines," J. Infect. Dis. 224(S4):S429-S442.

Haumont, M. et al. (1996). "Purification, Characterization and Immunogenicity of Recombinant Varicella-Zoster Virus Glycoprotein gE Secreted by Chinese Hamster Ovary Cells," Virus Res. 40(2):199-204.

International Preliminary Report on Patentability, issued Sep. 6, 2022, for PCT Application, PCT/US2021/021544, filed on Mar. 9, 2021, 8 pages.

International Search Report and Written Opinion, mailed on Jun. 4, 2021, for PCT Application No. PCT/US2021/021544, filed on Mar. 9, 2021, 12 pages.

Lal, H. et al. (2018). "Efficacy of an Adjuvanted Herpes Zoster Subunit Vaccine in Older Adults," N. Eng. J. Med. 372 (22):2087-2096.

Latimer, L.J.P. et al. (1995). "Specificity of Monoclonal Antibodies Produced Against Phosphorothioate and Ribo Modified DNAs," Mol. Immunol. 32(14/15):1057-1064.

Leroux-Roels, G. et al. (2016, e-pub. May 25, 2016). "Impact of Adjuvants on CD4+ T Cell and B Cell Responses to a Protein Antigen Vaccine: Results from a Phase II, Randomized, Multicenter Trial," Clin. Immunol. 169: 16-27.

Levin, M.J. et al. (2019, e-pub. Jan. 24, 2019). "Immune Responses to Zoster Vaccines," Human Vaccines & Immunotherapeutics 15(4):772-777.

Maltz, F. et al. (Jul./Aug. 2019). "Shingrix: a New Herpes Zoster Vaccine," P&T 44(7):406-433, 5 pages.

Pramanick, S. et al. (2013). "Excipient Selection In Parenteral Formulation Development," Pharma Times 45(3):65-77.

Schmader, K.E. et al. (2021). "Impact of Reactogenicity After Two Doses of Recombinant Zoster Vaccine Upon Physical Functioning and Quality of Life: An Open Phase III Trial in Older Adults," Journals of Gerontology: Medical Sciences 76(3):485-490.

Schwarz, T.F. et al. (2018, e-pub. Mar. 21, 2018). "Persistence of Immune Response to an Adjuvanted Varicella-Zoster Virus Subunit Vaccine for up to Year Nine in Older Adults," Human Vaccines & Immunotherapeutics 14(6):1370-1377.

Shah, R.R. et al. (2017). "Chapter 1: Overview of Vaccine Adjuvants: Introduction, History, and Current Status," Methods Mol. Biol. 1494:1-13.

SHINGRIX® (2021). "Highlights of Prescribing Information," Zoster Vaccine Recombinant, Adjuvanted, 24 pages.

VARIVAX® (Mar. 2020). "Frozen—Highlights of Prescribing Information," Varicella Virus Vaccine Live, 13 pages.

Vecchi, S. et al. (2012, e-pub. Sep. 14, 2011). "Aluminum Adjuvant Dose Guidelines in Vaccine Formulation for Preclinical Evaluations," Journal of Pharmaceuticals Sciences 101(1):17-20.

Voic, H. et al. (2020, e-pub. Nov. 23, 2020). "Identification and Characterization of CD4+ T Cell Epitopes After Shingrix Vaccination," J. Virol. 94(24)e01641-20, 22 pages.

Wang, Y. et al. (2021, e-pub. Aug. 5, 2020). "Immune Responses to Varicella-Zoster Virus Glycoprotein E Formulated with Poly(Lactic-co-Glycolic Acid) Nanoparticles and Nucleic Acid Adjuvants in Mice," Virologica Sinica 36:122-132.

ZOSTAVAX® (Mar. 2018). "Frozen—Highlights of Prescribing Information," Zoster Vaccine Live, 12 pages.

ZOSTAVAX® (Mar. 2018). "Liquid—Highlights of Prescribing Information," Zoster Vaccine Live, 12 pages.

Extended European Search Report, dated Feb. 27, 2024, for European Patent Application No. 21767529.7, 36 pages.

* cited by examiner

SEQUENCE LISTING

<160> NUMBER OF SEQ ID NOS: 5

<210> SEQ ID NO 1

```
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
tgactgtgaa cgttcgagat ga                                              22

<210> SEQ ID NO 2
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 7, 11
<223> OTHER INFORMATION: 2'-deoxy-7-deazaguanosine

<400> SEQUENCE: 2
tcgaacgttc g                                                          11

<210> SEQ ID NO 3
<211> LENGTH: 10
<212> TYPE: DNA
<213> ORGANISM: Artificial Sequence
<220> FEATURE:
<223> OTHER INFORMATION: Synthetic Construct

<400> SEQUENCE: 3
aacgttcgag                                                            10

<210> SEQ ID NO 4
<211> LENGTH: 546
<212> TYPE: PRT
<213> ORGANISM: Varicella zoster virus

<400> SEQUENCE: 4

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175
```

```
Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Ile Arg Tyr Ala Ala Trp Thr Gly Gly
    530                 535                 540

Leu Ala
545
```

<210> SEQ ID NO 5
<211> LENGTH: 537
<212> TYPE: PRT
<213> ORGANISM: Varicella zoster virus

<400> SEQUENCE: 5

-continued

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
                20                  25                  30

Leu Arg Tyr Asp Asp Phe His Thr Asp Glu Asp Lys Leu Asp Thr Asn
            35                  40                  45

Ser Val Tyr Glu Pro Tyr Tyr His Ser Asp His Ala Glu Ser Ser Trp
        50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
            115                 120                 125

Asp Thr Gly Ile His Val Ile Pro Thr Leu Asn Gly Asp Asp Arg His
        130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
            195                 200                 205

Thr Gly Asp Ala Ala Pro Ala Ile Gln His Ile Cys Leu Lys His Thr
        210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
            275                 280                 285

Leu Arg Thr Glu Lys Gln Tyr Leu Gly Val Tyr Ile Trp Asn Met Arg
        290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
            355                 360                 365

Glu Ala Pro Phe Asp Leu Leu Leu Glu Trp Leu Tyr Val Pro Ile Asp
        370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415
```

-continued

```
Ser Pro His Leu Ala Gln Arg Val Ala Ser Thr Val Tyr Gln Asn Cys
            420             425             430

Glu His Ala Asp Asn Tyr Thr Ala Tyr Cys Leu Gly Ile Ser His Met
        435             440             445

Glu Pro Ser Phe Gly Leu Ile Leu His Asp Gly Gly Thr Thr Leu Lys
    450             455             460

Phe Val Asp Thr Pro Glu Ser Leu Ser Gly Leu Tyr Val Phe Val Val
465             470             475             480

Tyr Phe Asn Gly His Val Glu Ala Val Ala Tyr Thr Val Val Ser Thr
            485             490             495

Val Asp His Phe Val Asn Ala Ile Glu Glu Arg Gly Phe Pro Pro Thr
        500             505             510

Ala Gly Gln Pro Pro Ala Thr Thr Lys Pro Lys Glu Ile Thr Pro Val
        515             520             525

Asn Pro Gly Thr Ser Pro Leu Leu Arg
    530             535
```

SHINGLES VACCINES COMPRISING A TLR9 AGONIST

CROSS-REFERENCE TO RELATED APPLICATIONS

This application is a national stage application under 35 U.S.C. § 371 of International Application No. PCT/US2021/021544, filed Mar. 9, 2021, which claims priority to and the benefit of U.S. Provisional Application No. 62/987,243, filed Mar. 9, 2020, the disclosure of each of which is incorporated herein by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 377882007100SEQLIST.TXT, date recorded: Sep. 8, 2022, size: 9,992 bytes).

FIELD

The present disclosure relates to immunogenic compositions comprising a varicella zoster virus surface (VZV) glycoprotein E antigen and a toll-like receptor 9 (TLR9) agonist, such as an oligonucleotide comprising an unmethylated cytidine-phospho-guanosine (CpG) motif. The immunogenic compositions are suitable for stimulating an immune response against VZV in an individual in need thereof.

BACKGROUND

Shingles (herpes zoster) is a viral disease characterized by a feeling of burning, tingling and itching on one side of the body or face, followed by a painful rash and blisters. According to the Center for Disease Control and Prevention (CDC), about 10-13% of older people with shingles experience long-term nerve pain (postherpetic neuralgia) as a complication. Additionally, a shingles rash near an eye or an ear may result in vision loss or cause muscles of the face to become paralyzed (Ramsay Hunt syndrome).

Shingles, like chicken pox, is caused by infection with varicella zoster virus (VZV). Shingles is caused by reactivation of latent VZV in an individual who had chickenpox as a result of an initial infection with VZV. Prior to U.S. Food and Drug Administration (FDA) approval of a varicella vaccine in 1995, most children in the U.S. contracted chickenpox and are therefore now at risk of contracting shingles as adults.

Two vaccines are available for prevention of herpes zoster in individuals who are 50 years of age or older. ZOSTAVAX® is a live attenuated virus vaccine marketed by Merck & Co., Inc. (Whitehouse Station, NJ). SHINGRIX® is a recombinant, adjuvanted subunit vaccine marketed by GlaxoSmithKline (Research Triangle Park, NC). Although no head-to-head clinical trials were conducted, the Advisory Committee on Immunization Practices narrowly voted in 2017 to recommend preferential use of SHINGRIX® over ZOSTAVAX® based on estimates of improved efficacy against herpes zoster and postherpetic neuralgia (Dooling et al., MMWR, 67:103-108, 2018). SHINGRIX® contains a recombinant VZV glycoprotein E (gE) as an antigen in combination with AS01B as the adjuvant. AS01B is composed of 3-O-desacyl-4'-monophosphoryl lipid A (MPL)

from *Salmonella minnesota* and QS-21, a saponin purified from an extract of Quillaja *saponaria* Molina, combined in a liposomal formulation. The narrow vote in favor of SHINGRIX® (8 to 7) was associated with concerns about reactogenicity. Phase III studies for SHINGRIX® reported that 16.5% of vaccine recipients developed grade 3 adverse events versus 3.1% of placebo recipients, and that 10.8% of vaccine recipients developed grade 3 systemic events (myalgia, fatigue, headache, shivering, fever, and gastrointestinal symptoms) versus 2.4% of placebo recipients (Lal et al., N Eng J Med, 372:2087-2096, 2015; and Cunningham et al., N Eng J Med, 375:1019-1032, 2016). The relatively high levels of serious side effects after SHINGRIX® vaccination was recognized as having the potential to negatively impact second dose compliance levels in patients (Bharucha et al., Human Vaccines & Immunotherapeutics, 13:1789-1797, 2017), and this has been a persistent concern given the need for a patient to receive both doses to be protected against shingles.

Reactogenicity of protein subunit vaccines such as SHINGRIX® can be influenced by a variety of factors, chief among which is the nature of the adjuvant included to improve immunogenicity. Different Adjuvant Systems (AS) adjuvants combined with a model protein antigen were compared by immunization of healthy, human subjects. The AS01B adjuvant was found to induce higher levels of local and systemic reactogenicity than the comparator adjuvants (AS01E, AS03A, AS04, and alum)(Leroux-Roels et al., Clin Immunol, 169:16-27, 2016). This suggests that AS01B is contributing significantly to the concerning reactogenicity profile of SHINGRIX.

Thus, there is a need for an improved Shingles vaccine with a superior safety profile, but which is not inferior to SHINGRIX® with regard to VZV gE immunogenicity.

SUMMARY

The present disclosure relates to immunogenic compositions comprising a varicella zoster virus surface (VZV) glycoprotein E antigen and a toll-like receptor 9 (TLR9) agonist, such as an oligonucleotide comprising an unmethylated cytidine-phospho-guanosine (CpG) motif. The immunogenic compositions are suitable for stimulating an immune response against VZV in individuals in need thereof.

GENERAL TECHNIQUES AND DEFINITIONS

Figure 1B:
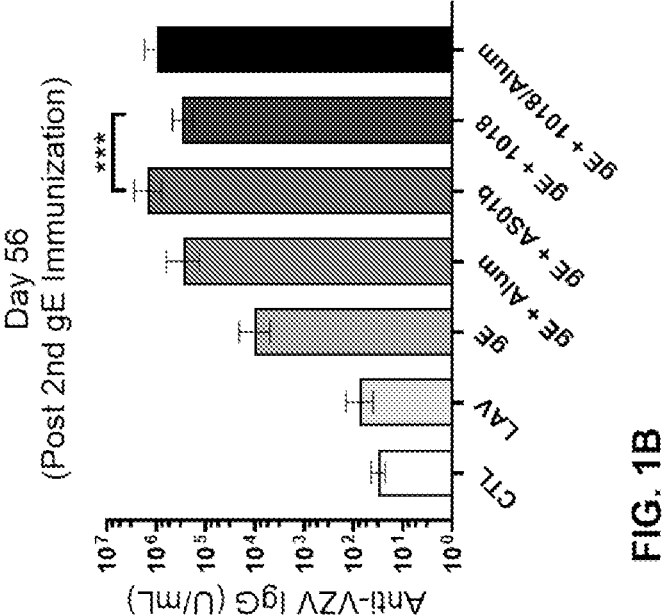
FIG. 1B shows the levels of anti-VZV gE-reactive IgG in sera of recipients of a first dose (prime) and a second dose (boost) of a shingles vaccine and control recipients (CTL and LAV).

The practice of the present disclosure will employ, unless otherwise indicated, conventional techniques of molecular biology (including recombinant techniques), microbiology, cell biology, biochemistry and immunology, which are within the skill of the art.

As used herein and in the appended claims, the singular forms "a", "an", and "the" include plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments.

The term "about" as used herein in reference to a value, encompasses from 90% to 110% of that value (e.g., about 3000 μg of CpG 1018 refers to 2700 μg to 3300 μg of CpG 1018).

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphodiester linkages, although alternate linkages, such as phosphorothioate esters may also be used in oligonucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, thymidine, and deoxycytidine. A nucleotide is a phosphate ester of a nucleoside.

The terms "CpG," "CpG motif," and "cytosine-phosphate-guanosine," as used herein, refer to an unmethylated cytidine-phospho-guanosine dinucleotide, which when present in an oligonucleotide contributes to a measurable immune response in vitro, in vivo and/or ex vivo. Examples of measurable immune responses include, but are not limited to, antigen-specific antibody production, secretion of cytokines, activation or expansion of lymphocyte populations, such as NK cells, CD4+ T lymphocytes, CD8+ T lymphocytes, B lymphocytes, and the like. Preferably, the CpG oligonucleotide preferentially activates a Th1-type response.

An "effective amount" or a "sufficient amount" of a substance is that amount sufficient to effect beneficial or desired results, including clinical results, and, as such, an "effective amount" depends upon the context in which it is being applied. In the context of administering an immunogenic composition, an effective amount contains sufficient antigen and TLR9 agonist to stimulate an immune response (preferably a seroprotective level of antibody to the antigen).

The terms "individual" and "subject" refer to mammals. "Mammals" include, but are not limited to, humans, non-human primates (e.g., monkeys), farm animals, sport animals, rodents (e.g., mice and rats), and pets (e.g., dogs and cats).

The term "dose" as used herein in reference to an immunogenic composition refers to a measured portion of the immunogenic composition taken by (administered to or received by) a subject at any one time.

The terms "isolated" and "purified" as used herein refers to a material that is removed from at least one component with which it is naturally associated (e.g., removed from its original environment). The term "isolated," when used in reference to a recombinant protein, refers to a protein that has been removed from the culture medium of the host cell that produced the protein.

"Stimulation" of a response or parameter includes eliciting and/or enhancing that response or parameter when compared to otherwise same conditions except for a parameter of interest, or alternatively, as compared to another condition (e.g., increase in TLR-signaling in the presence of a TLR agonist as compared to the absence of the TLR agonist). For example, "stimulation" of an immune response means an increase in the response. Depending upon the parameter measured, the increase may be from 5-fold to 500-fold or over, or from 5, 10, 50, or 100-fold to 500, 1,000, 5,000, or 10,000-fold.

As used herein the term "immunization" refers to a process that increases a mammalian subject's reaction to antigen and therefore improves its ability to resist or overcome infection and/or resist disease.

The term "vaccination" as used herein refers to the introduction of vaccine into a body of a mammalian subject.

"Adjuvant" refers to a substance which, when added to a composition comprising an antigen, enhances or potentiates an immune response to the antigen in the mammalian recipient upon exposure.

DETAILED DESCRIPTION

The present disclosure relates to immunogenic compositions comprising a varicella zoster virus (VZV) glycoprotein E (gE) antigen and a toll-like receptor 9 (TLR9) agonist, such as oligonucleotide comprising an unmethylated cytidine-phospho-guanosine (CpG) motif. The VZV gE antigen may be a truncated recombinant protein devoid of signal peptide, transmembrane and cytoplasmic domains of a full-length VZV gE antigen. The immunogenic compositions are suitable for stimulating an immune response against varicella zoster virus in an individual in need thereof.

I. Immunogenic Compositions and Kits

The present disclosure relates to immunogenic compositions for stimulating an immune response against varicella zoster virus (VZV), comprising a VZV glycoprotein E (gE) antigen and a toll-like receptor 9 (TLR9) agonist, wherein the TLR9 agonist is an oligonucleotide of from 8 to 35 nucleotides in length comprising an unmethylated cytidine-phospho-guanosine (also referred to as CpG or cytosine-phosphate-guanosine) motif, and the gE antigen and oligonucleotide are present in the immunogenic composition in amounts effective to stimulate an immune response against the gE antigen in a mammalian subject, such as a human) subject. In some embodiments, the immunogenic compositions further comprise an aluminum salt adjuvant to which the VZV gE antigen is adsorbed.

A. Toll-Like Receptor 9 (TLR9) Agonists

Toll-like receptors (TLRs) are expressed in and on dendritic cells and other innate immune cells and are among the most important receptors for stimulating a response to the presence of invading pathogens. Humans have multiple types of TLRs that are similar in structure but recognize different parts of viruses or bacteria. By activating specific TLRs, it is possible to stimulate and control specific types of innate immune responses that can be harnessed to enhance adaptive responses.

TLR9 (CD289) recognizes unmethylated cytidine-phospho-guanosine (CpG) motifs found in microbial DNA, which can be mimicked using synthetic CpG-containing oligodeoxynucleotides (CpG-ODNs). CpG-ODNs are known to enhance antibody production and to stimulate T helper 1 (Th1) cell responses (Coffman et al., Immunity, 33:492-503, 2010). Based on structure and biological function, CpG-ODNs have been divided into three general classes: CpG-A, CpG-B, and CpG-C(Campbell, Methods Mol Biol, 1494:15-27, 2017). The degree of B cell activation varies between the classes with CpG-A ODNs being weak, CpG-C ODNs being good, and CpG-B ODNs being strong B cell activators. Oligonucleotide TLR9 agonists of the present disclosure are preferably good B cell activators (CpG-C ODN) or more preferably strong (CpG-B ODN) B cell activators.

Optimal oligonucleotide TLR9 agonists often contain a palindromic sequence following the general formula of: 5'-purine-purine-CG-pyrimidine-pyrimidine-3', or 5'-purine-purine-CG-pyrimidine-pyrimidine-CG-3' (U.S. Pat. No. 6,589,940). TLR9 agonism is also observed with certain non-palindromic CpG-enriched phosphorothioate oligonucleotides, but may be affected by changes in the nucleotide sequence. Additionally, TLR9 agonism is abolished by methylation of the cytosine within the CpG dinucleotide. Accordingly in some embodiments, the TLR9 agonist is an oligonucleotide of from 8 to 35 nucleotides in length comprising the sequence 5'-AACGTTCG-3'. In some embodiments, the oligonucleotide is greater than 8, 9, 10, 11, 12, 13, 14, 15, 16, 17, 18, 19, or 20 nucleotides in length, and the oligonucleotide is less than 35, 34, 33, 32, 31, 30, 29, 28, 27, 26, 25, or 24 nucleotides in length. In some embodiments, the TLR9 agonist is an oligonucleotide of from 10 to 35 nucleotides in length comprising the sequence 5'-AACGTTCGAG-3' (SEQ ID NO:3). In some embodiments, the oligonucleotide is greater than 10, 11, 12, 13, 14, 15, 16, 17, 18, 19, or 20 nucleotides in length, and the oligonucleotide is less than 35, 34, 33, 32, 31, 30, 29, 28, 27, 26, 25, or 24 nucleotides in length.

Researchers at Dynavax Technologies Corporation (Emeryville, CA) have identified a 22-mer phosphorothioate linked oligodeoxynucleotide, CpG 1018, which contains specific sequences that can substantially enhance the immune response to co-administered antigens across species (Campbell, Methods Mol Biol, 1494:15-27, 2017). CpG 1018 (5'-TGACTGTGAA CGTTCGAGAT GA-3', set forth as SEQ ID NO:1) was chosen after screening a broad panel of oligonucleotides for immunostimulatory activity in vitro and in vivo. CpG 1018 is a CpG-B ODN that is active in mice, rabbits, dogs, baboons, cynomolgus monkeys, and humans. Thus in some preferred embodiments, the TLR9 agonist is an oligonucleotide comprising the sequence of SEQ ID NO:1.

Although the exemplary oligonucleotide TLR9 agonist, CpG 1018, is a CpG-ODN, the present disclosure is not restricted to fully DNA molecules. That is, in some embodiments, the TLR9 agonist is a DNA/RNA chimeric molecule in which the CpG(s) and the palindromic sequence are deoxyribonucleic acids and one or more nucleic acids outside of these regions are ribonucleic acids. In some embodiments, the CpG oligonucleotide is linear. In other embodiments, the CpG oligonucleotide is circular or includes hairpin loop(s). The CpG oligonucleotide may be single stranded or double stranded.

In some embodiments, the CpG oligonucleotide may contain modifications. Modifications include but are not limited to, modifications of the 3'OH or 5'OH group, modifications of the nucleotide base, modifications of the sugar component, and modifications of the phosphate group. Modified bases may be included in the palindromic sequence of the CpG oligonucleotide as long as the modified base(s) maintains the same specificity for its natural complement through Watson-Crick base pairing (e.g., the palindromic portion is still self-complementary). In some embodiments, the CpG oligonucleotide comprises a non-canonical base. In some embodiments, the CpG oligonucleotide comprises a modified nucleoside. In some embodiments, the modified nucleoside is selected from the group consisting of 2'-deoxy-7-deazaguanosine, 2'-deoxy-6-thioguanosine, arabinoguanosine, 2'-deoxy-2'substituted-arabinoguanosine, and 2'-O-substituted-arabinoguanosine. In some embodiments, the TLR9 agonist is an oligonucleotide comprising the sequence 5'-TCG$_1$AACG$_1$TTCG$_1$-3' (SEQ ID NO:2), in which G$_1$ is 2'-deoxy-7-deazaguanosine. In some embodiments, the oligonucleotide comprises the sequence 5'-TCG$_1$AACG$_1$TTCG$_1$-X-G$_1$CTTG$_1$CAAG$_1$CT-5', and in which G$_1$ is 2'-deoxy-7-deazaguanosine and X is glycerol (5'-SEQ ID NO:2-3'-X-3'-SEQ ID NO:2-5').

The CpG oligonucleotide may contain a modification of the phosphate group. For example, in addition to phosphodiester linkages, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. In some embodiments, the oligonucleotides comprise only phosphorothioate backbones. In some embodiments, the oligonucleotides comprise only phosphodiester backbones. In some embodiments, the oligonucleotide comprises a combination of phosphate linkages in the phosphate backbone such as a combination of phosphodiester and phosphorothioate linkages. Oligonucleotides with phosphorothioate backbones can be more immunogenic than those with phosphodiester backbones and appear to be more resistant to degradation after injection into the host (Braun et al., J Immunol, 141:2084-2089, 1988; and Latimer et al., Mol Immunol, 32:1057-1064, 1995). The CpG oligonucleotides of the present disclosure include at least one, two or three internucleotide phosphorothioate ester linkages. In some embodiments, when a plurality of CpG oligonucleotide molecules are present in a pharmaceutical composition comprising at least one excipient, both stereoisomers of the phosphorothioate ester linkage are present in the plurality of CpG oligonucleotide molecules. In some embodiments, all of the internucleotide linkages of the CpG oligonucleotide are phosphorothioate linkages, or said another way, the CpG oligonucleotide has a phosphorothioate backbone.

A unit dose of the immunogenic composition, which is typically a 0.5 ml dose, may comprises from about 375 μg to about 6000 μg of the CpG oligonucleotide, preferably from about 750 μg to about 3000 μg of the CpG oligonucleotide. In some embodiments, a 0.5 ml dose of the immunogenic composition comprises greater than about 250, 500, 750, 1000, or 1250 μg of the CpG oligonucleotide, and less than about 6000, 5000, 4000, 3000, or 2000 μg of the CpG oligonucleotide. In some embodiments, a 0.5 ml dose of the immunogenic composition comprises about 375, 750, 1500, 3000 or 6000 μg of the CpG oligonucleotide. In some embodiments, a 0.5 ml dose of the immunogenic composition comprises about 750 μg of the CpG oligonucleotide. In some embodiments, a 0.5 ml dose of the immunogenic composition comprises about 1500 μg of the CpG oligonucleotide. In some embodiments, a 0.5 ml dose of the immunogenic composition comprises about 3000 μg of the CpG oligonucleotide.

The CpG oligonucleotides described herein are in their pharmaceutically acceptable salt form unless otherwise indicated. Exemplary basic salts include ammonium salts, alkali metal salts such as sodium, lithium, and potassium salts, alkaline earth metal salts such as calcium and magnesium salts, zinc salts, salts with organic bases (for example, organic amines) such as N-Me-D-glucamine, N-[1-(2,3-dioleoyloxy)propyl]-N,N,N-trimethylammonium chloride, choline, tromethamine, dicyclohexylamines, t-butyl amines, and salts with amino acids such as arginine, lysine and the like. In some embodiment, the CpG oligonucleotides are in the ammonium, sodium, lithium, or potassium salt form. In one preferred embodiment, the CpG oligonucleotides are in the sodium salt form.

B. Varicella Zoster Virus (VZV) Glycoprotein E (gE) Antigen

A VZV gE antigen of the immunogenic compositions of the present disclosure comprises gE or a fragment thereof. In preferred embodiments, the gE antigen is recognized by VZV-reactive antibodies and/or peptide fragments of gE are recognized by VZV-reactive T cells. In some embodiments, the gE antigen is a recombinant protein, while in other embodiments the gE antigen is a purified from VZV virions. In some preferred embodiments, the gE antigen is an isolated antigen. In some embodiments, the VZV gE antigen is a truncated recombinant protein devoid of signal peptide, transmembrane and cytoplasmic domains of a full-length VZV gE antigen. The amino acid sequence of a representative gE is set forth as GenBank No. AQT34120.1. In some embodiments, the gE antigen comprises the amino acid sequence from residues 39-585 of GenBank No. AQT34120.1, or the amino acid sequence that is at least 90%, 95%, 96%, 97%, 98% or 99% identical thereto.

In some embodiments, the amino acid sequence of the gE is set forth as SEQ ID NO:4:

```
MGTVNKPVVG VLMGFGIITG TLRITNPVRA SVLRYDDFHI

DEDKLDTNSV YEPYYHSDHA ESSWVNRGES SRKAYDHNSP

YIWPRNDYDG FLENAHEHHG VYNQGRGIDS GERLMQPTQM

SAQEDLGDDT GIHVIPTLNG DDRHKIVNVD QRQYGDVFKG

DLNPKPQGQR LIEVSVEENH PFTLRAPIQR IYGVRYTETW

SFLPSLTCTG DAAPAIQHIC LKHTTCFQDV VVDVDCAENT

KEDQLAEISY RFQGKKEADQ PWIVVNTSTL FDELELDPPE

IEPGVLKVLR TEKQYLGVYI WNMRGSDGTS TYATFLVTWK

GDEKTRNPTP AVTPQPRGAE FHMWNYHSHV FSVGDTFSLA

MHLQYKIHEA PFDLLLEWLY VPIDPTCQPM RLYSTCLYHP

NAPQCLSHMN SGCTFTSPHL AQRVASTVYQ NCEHADNYTA

YCLGISHMEP SFGLILHDGG TTLKFVDTPE SLSGLYVFVV

YFNGHVEAVA YTVVSTVDHF VNAIEERGFP PTAGQPPATT

KPKEITPVNP GTSPLIRYAA WTGGLA.
```

In some embodiments, the gE antigen comprises the amino acid sequence of SEQ ID NO:4, or the amino acid sequence that is at least 90%, 95%, 96%, 97%, 98% or 99% identical to SEQ ID NO:4.

In some embodiments, the amino acid sequence of the gE is set forth as SEQ ID NO:5:

```
MGTVNKPVVG VLMGFGIITG TLRITNPVRA SVLRYDDFHT

DEDKLDTNSV YEPYYHSDHA ESSWVNRGES SRKAYDHNSP

YIWPRNDYDG FLENAHEHHG VYNQGRGIDS GERLMQPTQM

SAQEDLGDDT GIHVIPTLNG DDRHKIVNVD QRQYGDVFKG

DLNPKPQGQR LIEVSVEENH PFTLRAPIQR IYGVRYTETW

SFLPSLTCTG DAAPAIQHIC LKHTTCFQDV VVDVDCAENT

KEDQLAEISY RFQGKKEADQ PWIVVNTSTL FDELELDPPE

IEPGVLKVLR TEKQYLGVYI WNMRGSDGTS TYATFLVTWK

GDEKTRNPTP AVTPQPRGAE FHMWNYHSHV FSVGDTFSLA

MHLQYKIHEA PFDLLLEWLY VPIDPTCQPM RLYSTCLYHP

NAPQCLSHMN SGCTFTSPHL AQRVASTVYQ NCEHADNYTA

YCLGISHMEP SFGLILHDGG TTLKFVDTPE SLSGLYVFVV

YFNGHVEAVA YTVVSTVDHF VNAIEERGFP PTAGQPPATT

KPKEITPVNP GTSPLLR.
```

In some embodiments, the gE antigen comprises the amino acid sequence of SEQ ID NO:5, or the amino acid sequence that is at least 90%, 95%, 96%, 97%, 98% or 99% identical to SEQ ID NO:5.

A unit dose of the immunogenic composition, which is typically a 0.5 ml dose, may comprise from about 10 μg to about 100 μg of the gE antigen, preferably from about 25 μg to about 75 μg of the gE antigen, preferably about 40 to about 60 μg of the gE antigen, or about 50 ng of the gE antigen.

C. Additional Components

The immunogenic compositions of the present disclosure may comprise one or more additional components, such as one or more excipients, another adjuvant, and/or additional antigens.

1. Excipients

Pharmaceutically acceptable excipients of the present disclosure include for instance, solvents, bulking agents, buffering agents, tonicity adjusting agents, and preservatives (Pramanick et al., Pharma Times, 45:65-77, 2013). In some embodiments the immunogenic compositions may comprise an excipient that functions as one or more of a solvent, a bulking agent, a buffering agent, and a tonicity adjusting agent (e.g., sodium chloride in saline may serve as both an aqueous vehicle and a tonicity adjusting agent).

In some embodiments, the immunogenic compositions comprise an aqueous vehicle as a solvent. Suitable vehicles include for instance sterile water, saline solution, phosphate buffered saline, and Ringer's solution. In some embodiments, the composition is isotonic.

The immunogenic compositions may comprise a buffering agent. Buffering agents control pH to inhibit degradation of the active agent during processing, storage and optionally reconstitution. Suitable buffers include for instance salts comprising acetate, citrate, phosphate or sulfate. Other suitable buffers include for instance amino acids such as arginine, glycine, histidine, and lysine. The buffering agent may further comprise hydrochloric acid or sodium hydroxide. In some embodiments, the buffering agent maintains the pH of the composition within a range of 6 to 9. In some embodiments, the pH is greater than (lower limit) 6, 7 or 8. In some embodiments, the pH is less than (upper limit) 9, 8, or 7. That is, the pH is in the range of from about 6 to 9 in which the lower limit is less than the upper limit.

The immunogenic compositions may comprise a tonicity adjusting agent. Suitable tonicity adjusting agents include for instance dextrose, glycerol, sodium chloride, glycerin and mannitol.

The immunogenic compositions may comprise a bulking agent. Bulking agents are particularly useful when the pharmaceutical composition is to be lyophilized before administration. In some embodiments, the bulking agent is a protectant that aids in the stabilization and prevention of degradation of the active agents during freeze or spray drying and/or during storage. Suitable bulking agents are sugars (mono-, di- and polysaccharides) such as sucrose, lactose, trehalose, mannitol, sorbital, glucose and raffinose.

The immunogenic compositions may comprise a preservative. Suitable preservatives include for instance antioxidants and antimicrobial agents. However, in preferred embodiments, the immunogenic composition is prepared under sterile conditions and is in a single use container, and thus does not necessitate inclusion of a preservative.

2. Additional Adjuvants

Adjuvants are known in the art and include, but are not limited to, alum (aluminum salts), oil-in-water emulsions, water-in-oil emulsions, liposomes, and microparticles, such as poly(lactide-co-glycolide) microparticles (Shah et al., Methods Mol Biol, 1494:1-14, 2017). In some embodiments, the immunogenic compositions further comprises an aluminum salt adjuvant to which the gE antigen is adsorbed. In some embodiments, the aluminum salt adjuvant comprises one or more of the group consisting of amorphous aluminum hydroxyphosphate sulfate, aluminum hydroxide, aluminum phosphate, and potassium aluminum sulfate. In some embodiments, the aluminum salt adjuvant comprises one or both of aluminum hydroxide and aluminum phosphate. In some embodiments, the aluminum salt adjuvant consists of aluminum hydroxide. In some embodiments, a unit dose (e.g., about 0.5 ml) of the immunogenic composition comprises from about 0.25 to about 0.50 mg $Al^{3+}$, preferably from about 0.30 to about 0.40 mg $Al^{3+}$.

In other embodiments, the immunogenic composition further comprises an additional adjuvant. Additional suitable adjuvants include, but are not limited to, squalene-in-water emulsions (e.g., MF59 or AS03), TLR3 agonists (e.g., poly-IC or poly-ICLC), TLR4 agonists (e.g., saponins such as Quil A or QS-21, as in AS01 or AS02), TLRS agonists (bacterial flagellin), and TLR7 and/or TLR8 agonists (imidazoquinoline derivatives such as imiquimod, and resiquimod)(Coffman et al., Immunity, 33:492-503, 2010). For veterinary use and for production of antibodies in non-human animals, mitogenic components of Freund's adjuvant (both complete and incomplete) can be used.

D. Kits

The present disclosure also provides kits comprising: i) an immunogenic composition comprising a VZV gE antigen and a toll-like receptor 9 (TLR9) agonist, such as a CpG oligonucleotide; and ii) a set of instructions for administration of the immunogenic composition to stimulate an immune response against the gE antigen in a mammalian subject, such as a human subject in need thereof. Additionally, the present disclosure provides kits comprising: i) a first composition comprising a VZV gE antigen; ii) a second composition comprising a TLR9 agonist, such as a CpG oligonucleotide; iii) instructions for mixing the first composition with the second composition to prepare an immunogenic composition; and optionally iv) a further set of instructions for administration of the immunogenic composition to stimulate an immune response against the gE antigen in a mammalian, such as a human subject in need thereof. In some embodiments, the CpG oligonucleotide comprises the sequence 5'-AACGTTCG-3'. In some embodiments, the CpG oligonucleotide comprises the sequence 5'-AACGTTCGAG-3' (SEQ ID NO:3). In some preferred embodiments, the CpG oligonucleotide comprises the sequence of 5'-TGACTGTGAA CGTTCGAGAT GA-3' (SEQ ID NO:1).

The kits may comprise an immunogenic composition packaged appropriately. For example, if the immunogenic composition is a freeze-dried power, a vial with a resilient stopper is normally used so that the powder may be easily resuspended by injecting fluid (e.g., sterile water, saline, etc.) through the resilient stopper. In some embodiments, the kits comprise a device for administration (e.g., syringe and needle). The instructions relating to the use of the immunogenic composition generally include information as to dosage, schedule and route of administration for the intended methods of use. In some embodiments, the immunogenic compositions are for stimulating an immune response against VZV.

II. Methods Of Use

The present disclosure relates to methods for stimulating an immune response against VZV, comprising: administering an immunogenic composition comprising a VZV glycoprotein E (gE) antigen and a Toll-like receptor 9 (TLR9) agonist, such as a CpG oligonucleotide, to a mammalian subject so as to stimulate an immune response against the gE antigen in the mammalian subject. In preferred embodiments, the immunogenic compositions are to be administered by intramuscular injection, optionally in a volume of about 0.5 mL (e.g., unit dose). In some embodiments, the intramuscular injection is into the deltoid muscle of the upper arm of a human subject in need thereof.

Stimulating an immune response, means increasing the immune response, which can arise from eliciting a de novo immune response (e.g., as a consequence of an initial vaccination regimen) or enhancing an existing immune response (e.g., as a consequence of a booster vaccination regimen). In some embodiments, stimulating an immune response includes but is not limited to one or more of the group consisting of: stimulating cytokine production; stimulating B lymphocyte proliferation; stimulating antibody production; stimulating interferon pathway-associated gene expression; stimulating chemoattractant-associated gene expression; and stimulating plasmacytoid dendritic cell maturation. In some preferred embodiments, stimulating an immune response comprises increasing an antigen-specific antibody response in the subject.

Enumerated Embodiments

1. An immunogenic composition for stimulating an immune response against a varicella zoster virus (VZV), comprising a VZV glycoprotein E (gE) antigen and a toll-like receptor 9 (TLR9) agonist, wherein the TLR9 agonist is an oligonucleotide of from 10 to 35 nucleotides in length comprising an unmethylated cytidine-phospho-guanosine (CpG) motif, and the gE antigen and the oligonucleotide are present in the immunogenic composition in amounts effective to stimulate an immune response against the gE antigen in a mammalian subject.

2. The composition of embodiment 1, wherein the oligonucleotide comprises the sequence 5'-AACGTTCGAG-3' (SEQ ID NO:3).

3. The composition of embodiment 1, wherein the oligonucleotide comprises the sequence of 5'-TGACTGTGAA CGTTCGAGAT GA-3'(SEQ ID NO:1).

4. The composition of any one of embodiments 1-3, wherein the oligonucleotide comprises a modified nucleoside, optionally wherein the modified nucleoside is selected from the group consisting of 2'-deoxy-7-deazaguanosine, 2'-deoxy-6-thioguanosine, arabinoguanosine, 2'-deoxy-2'substituted-arabinoguanosine, and 2'-O-substituted-arabinoguanosme.

5. The composition of embodiment 4, wherein the oligonucleotide comprises the sequence 5'-$TCG_1AACG_1TTCG_1$-3' (SEQ ID NO:2) in which $G_1$ is 2'-deoxy-7-deazaguanosine, optionally wherein the oligonucleotide comprises the sequence 5'-$TCG_1AACG_1TTCG_1$-X-$G_1CTTG_1CAAG_1CT$-5', and in which $G_1$ is 2'-deoxy-7-deazaguanosine and X is glycerol (5'-SEQ ID NO:2-3'-X-3'-SEQ ID NO:2-5').

6. The composition of any one of embodiments 1-5, wherein the oligonucleotide comprises at least one phosphorothioate linkage, optionally wherein all nucleotide linkages are phosphorothioate linkages.

7. The composition of any one of embodiments 1-6, wherein the oligonucleotide is a single-stranded oligodeoxynucleotide.

8. The composition of any one of embodiments 1-7, wherein a 0.5 ml dose of the immunogenic composition comprises from about 375 μg to about 6000 μg of the oligonucleotide or from about 750 μg to about 3000 μg of the oligonucleotide, optionally wherein a 0.5 ml dose of the immunogenic composition comprises about 375 μg, about 750 μg, about 1500 μg, about 3000 μg, or 6000 μg about of the oligonucleotide.

9. The composition of any one of embodiments 1-8, wherein the VZV gE antigen is a truncated, recombinant protein devoid of signal peptide, transmembrane and cytoplasmic domains of a full-length VZV gE antigen, optionally wherein the VZV gE antigen comprises:

(i) the amino acid sequence of residues 39-585 of Gen-Bank No. AQT34120.1, or the amino acid sequence that is at least 90%, 95%, 96%, 97%, 98% or 99% identical thereto; or (ii) the amino acid sequence of SEQ ID NO:4, or the amino acid sequence that is at least 90%, 95%, 96%, 97%, 98% or 99% identical to SEQ ID NO:4; or (iii) the amino acid sequence of SEQ ID NO:5, or the amino acid sequence that is at least 90%, 95%, 96%, 97%, 98% or 99% identical to SEQ ID NO:5.

10. The composition of any one of embodiments 1-9, wherein a 0.5 ml dose of the immunogenic composition comprises from about 25 to about 75 μg of the gE antigen, optionally wherein the immunogenic composition comprises from about 40 to about 60 μg of the gE antigen, or about 50 μg of the gE antigen.

11. The composition of any one of embodiments 1-10, further comprising an aluminum salt adjuvant.

12. The composition of embodiment 11, wherein the aluminum salt adjuvant comprises one or more of the group consisting of amorphous aluminum hydroxyphosphate sulfate, aluminum hydroxide, aluminum phosphate, and potassium aluminum sulfate.

13. The composition of embodiment 11, wherein the aluminum salt adjuvant comprises aluminum hydroxide.

14. The composition of any one of embodiments 11-13, wherein a 0.5 ml dose of the immunogenic composition comprises from about 0.25 to about 0.50 mg $Al^{3+}$, optionally wherein a 0.5 ml dose of the immunogenic composition comprises from about 0.30 to about 0.40 mg $Al^{3+}$.

15. The composition of any one of embodiments 1-14, wherein the mammalian subject is a human subject.

16. A kit comprising:

i) the immunogenic composition of any one of embodiments 1-15, and ii) instructions for administration of the composition to stimulate an immune response against the gE antigen in the mammalian subject.

17. A kit comprising:

i) a first composition comprising glycoprotein E (gE) antigen of a varicella zoster virus; ii) a second composition comprising a TLR9 agonist; and iii) instructions for mixing the first composition with the second composition to prepare an immunogenic composition.

18. The kit of embodiment 17, further comprising:

iv) a further set of instructions for administration of the immunogenic composition to stimulate an immune response against the gE antigen in a mammalian subject.

19. The kit of any one of embodiments 16-18, further comprising a syringe and needle for intramuscular injection of the immunogenic composition.

20. A method for stimulating an immune response against varicella zoster virus (VZV) in a mammalian subject, comprising administering the immunogenic composition of any one of embodiments 1-15 to a mammalian subject so as to stimulate an immune response against the gE antigen in the mammalian subject.

21. The method of embodiment 20, wherein the immunogenic composition is administered by intramuscular injection.

EXAMPLES

Abbreviations: CpG (unmethylated cytidine-phosphoguanosine); CTRL (control); gE (VZV glycoprotein E); LAV (live attenuated virus); mcg (microgram); mcl (microliter); MPL (monophosphoryl lipid A); TLR9 (toll-like receptor 9); and VZV (varicella zoster virus).

Example 1

Immunogenicity of CpG-Adjuvanted Zoster Vaccine in Mice

This example provides a description of a preclinical study to assess immunogenicity of zoster vaccines in mice infected with a live, attenuated varicella zoster virus (VZV) strain (referred to below as LAV).

Antigen: Recombinant VZV glycoprotein E (gE) is obtained by cell culture of genetically engineered Chinese Hamster Ovary host cells expressing a truncated version of gE lacking the transmembrane anchor and carboxy-terminal domain, and is therefore secreted into the supernatant. The cell culture is supported by media containing amino acids, but no albumin, antibiotics or animal derived proteins. gE is purified by chromatography and lyophilized for future use as described (Haumont et al., Virus Res, 40:199-204, 1996). For initial preclinical studies, VZV gE was obtained commercially.

Vaccines were prepared before use by combining gE with either an adjuvant formulation or a pharmaceutically acceptable buffer or normal saline. Specifically, gE was adsorbed to alum (aluminum hydroxide) for 30 min prior to injection, and AS01B and CpG 1018 adjuvants were each mixed with gE immediately prior to injections.

Experimental Design: The adjuvant activity of CpG 1018 was assessed in C57BL/6 mice (n=4-8/group) primed with a live attenuated VZV vaccine ($10^4$ plaque forming units of LAV in 500 mcl administered by the subcutaneous route) 35 days prior (day −35) to the start of the immunization schedule. The LAV used was the VARIVAX® varicella virus vaccine live marketed by Merck & Co., Inc. (Whitehouse Station, NJ). As mice do not support sufficient replication of VZV, this was done to mimic existing VZV infection in humans. Mice were immunized with 50 mcl of a vaccine formulation or a saline control by the intramuscular route on days 0 and 28. Groups, dosing amounts and sampling are listed in Table 1-1.

TABLE 1-1

Vaccination Groups for Evaluation of gE Immunogenicity

| Group | LAV Vaccine (Day-35) | Subunit Vaccine (Day 0 and 28) | # Mice | Bleed(s) | Sacrifice |
|---|---|---|---|---|---|
| 1 | None | None (Saline only control) | 4 | Day 56 | Day 56 |
| 2 | LAV | None (LAV only control) | 8 | Day 21, 56 | Day 56 |
| 3 | LAV | gE (5 mcg) | 8 | Day 21, 56 | Day 56 |
| 4 | LAV | gE (5 mcg) + alum (50 mcg) | 8 | Day 21, 56 | Day 56 |
| 5 | LAV | gE (5 mcg) + AS01b (50 mcL) | 8 | Day 21, 56 | Day 56 |
| 6 | LAV | gE (5 mcg) + CpG 1018 (10 mcg) | 8 | Day 21, 56 | Day 56 |
| 7 | LAV | gE (5 mcg) + CpG 1018 (10 mcg) + alum (50 mcg) | 8 | Day 21, 56 | Day 56 |

VZV gE contains both B cell and T cell epitopes. Accordingly, serum antibody responses to gE were measured with a commercially available ELISA using VZV gE antigen-coated microtiter plates following administration of 1 (day 21) or 2 doses (day 56) of vaccine. CD3$^+$CD4$^+$ T cell cytokine responses (IL-2 and IFN-γ) were measured by flow cytometry after in vitro re-stimulation of spleen cell cultures with overlapping peptides spanning the length of the gE antigen. Three spleen cell sub-pools per group were tested (3, 3, or 2 mouse spleens/pool). T cell responses were evaluated as percentage of CD4$^+$ T cells or as a percentage of CD154$^+$CD4$^+$ T cells, where CD154 is a molecule transiently up-regulated in antigen-stimulated cells and thus serves as a specific marker of antigen-reactive CD4$^+$ T cells (i.e., cells responding to gE peptide stimulation ex vivo). Mice were monitored for health parameters, including injection site reactions, and general appearance.

Figure 1A:
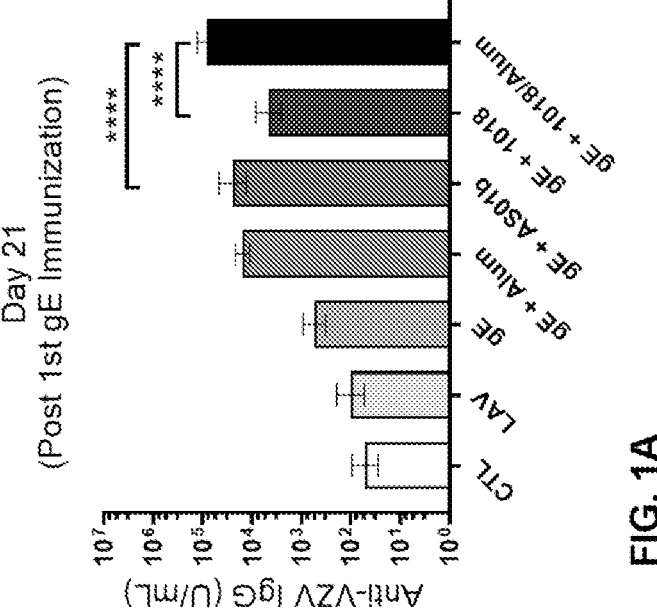
FIG. 1A shows the levels of anti-VZV gE-reactive IgG in sera of recipients of a first dose (prime) of a shingles vaccine and control recipients (CTL and LAV).

All adjuvant groups tested induced high levels of anti-VZV IgG response after prime and booster vaccinations. On Day 21 post 1$^{st}$ gE immunization (prime), anti-VZV IgG responses were elevated compared to background levels observed in non-immunized mice and mice that were LAV-primed but not further immunized. Addition of the adjuvants aluminum hydroxide (alum) alone or CpG 1018 alone increased the anti-VZV IgG response compared to immunization with gE antigen alone. The highest anti-VZV IgG responses post 1$^{st}$ immunization was observed in mice immunized with CpG-1018+alum (FIG. 1A). Responses in the gE+CpG 1018+alum immunized group were significantly higher than in mice immunized with gE in combination with CpG-1018 alone or mice immunized with gE+AS01b. Anti-VZV IgG responses were observed to be about one log higher post 2$^{nd}$ immunization (boost) on Day 56 in all gE±adjuvants groups (FIG. 1B), at which point comparable responses were seen in gE+AS01b and gE+CpG 1018+alum groups and the response in gE+AS01b immunized mice was significantly higher than in mice immunized with gE+CpG 1018 (ANOVA with Tukey's multiple comparisons test, * P<0.001, ** P<0.0001).

Figure 2C:
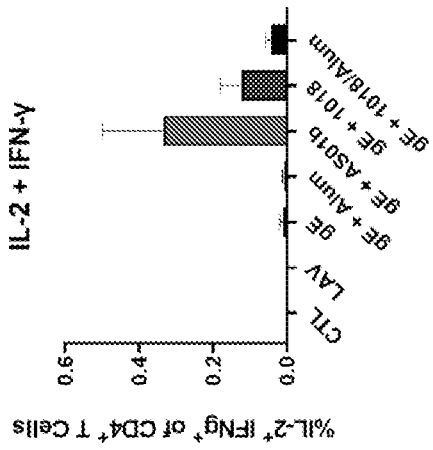
FIG. 2A-2C show gE-antigen induced, IL-2 and/or IFN-γ secreting CD4+ T cells of recipients of a first dose (prime) and a second dose (boost) of a shingles vaccine and control recipients (CTL and LAV).
Figure 2B:
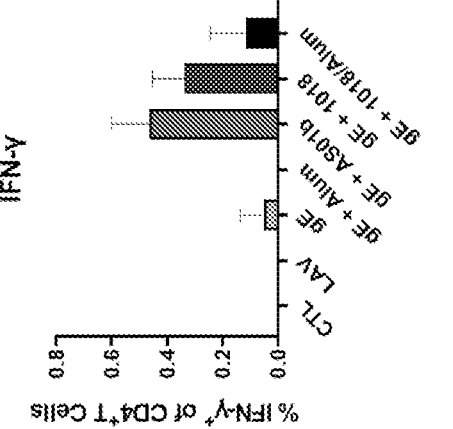
Figure 2A:
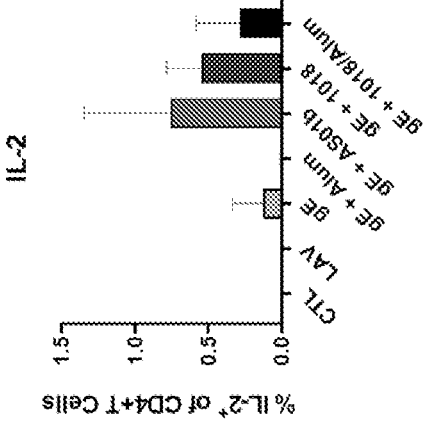
Figure 3B:
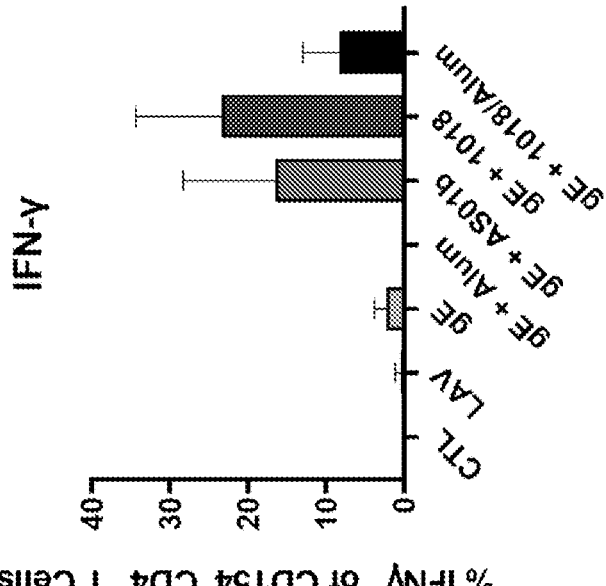
FIG. 3A-3B show gE-antigen induced, IL-2 or IFN-γ secreting CD154+, CD4+ T cells of recipients of a first dose (prime) and a second dose (boost) of a shingles vaccine and control recipients (CTL and LAV).
Figure 3A:
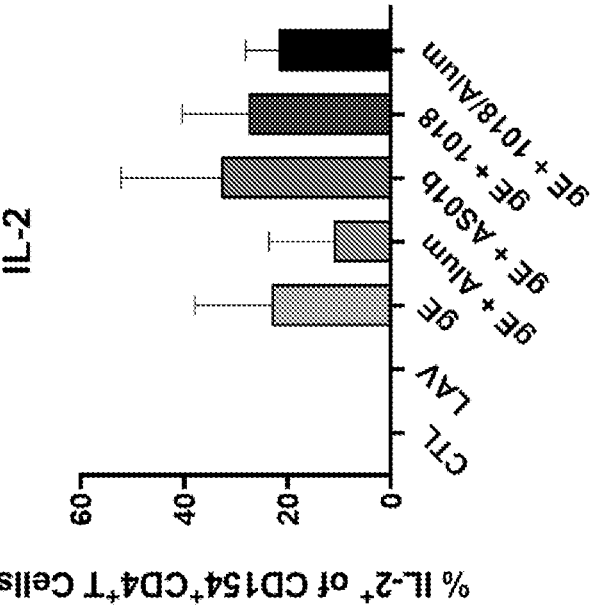

Ex vivo intracellular cytokine expression responses in gE peptides-stimulated spleen cells were quantified as a measure of the effect of immunization regimens on gE antigen-specific CD4$^+$ T cell responses. gE-stimulated cytokine expression was measured as a percentage of all CD4$^+$ T cells and as a percentage of the antigen-reactive population (CD154$^+$CD4$^+$ T cells). IL-2 and IFN-γ expression was absent or at very low levels in CD4+ T cells from the control (CTL), LAV-primed only, gE only and alum adjuvanted groups. In contrast, use of AS01b or CpG 1018 as adjuvants induced comparably elevated IL-2 (FIG. 2A) and IFN-γ expressing (FIG. 2B) T cells as measured after ex vivo re-stimulation. IL-2 and IFN-γ expression trended lower in re-stimulated CD4$^+$ T cells from gE+CpG 1018+alum-immunized groups. IL-2 and IFN-γ co-expressing CD4+ T cells were highest in cells from AS01b-adjuvanted mice, followed by cells from CpG 1018 and CpG 1018+alum-adjuvanted mice (FIG. 2C). The pattern of response was similar within the antigen-reactive (CD154$^+$) CD4+ T cell populations with comparable cytokine expression in gE peptides re-stimulated T cells from AS01b and CpG 1018-adjuvanted mice (FIG. 3A-3B). IFN-γ expression trended higher in antigen-specific T cells from CpG 1018 adjuvanted mice, as compared to T cells from AS01b adjuvanted mice, and both intracellular IL-2 and IFN-γ expression were lower in mice in which CpG 1018+alum was used to adjuvant gE responses.

In summary, all adjuvants tested induced high levels of anti-VZV IgG responses in C57BL/6 mice with the highest antibody responses in gE+CpG 1018+alum immunized mice after a first immunization, and in gE+AS01b-immunized mice after the booster immunization, although the levels induced in CpG 1018+alum were comparable. CD4$^+$ T cell responses to gE immunizations were evaluated following ex vivo gE peptides re-stimulations and the highest responses were observed in the CpG 1018 and AS01b-adjuvanted groups when measured as a percentage of all CD4$^+$ cells of the antigen-reactive population, as identified by expression of CD154. The data demonstrated that CpG 1018 in combination with alum or CpG 1018 as a stand-alone adjuvant induced comparable antibody and T cell responses, respectively, to AS01b in immunized mice. As T cell responses are believed to be primarily responsible for control of shingles outbreaks, the data support use of CpG 1018 as an adjuvant in a gE-based vaccine. CpG 1018 alone or in combination with alum is contemplated to generate a favorable reactogenicity profile in comparison to AS01b.

Although the foregoing disclosure has been described in some detail by way of illustration and example for purposes of clarity and understanding, it will be apparent to those skilled in the art that certain changes and modifications may be practiced. Therefore, the examples should not be construed as limiting the scope of the disclosure, which is delineated by the appended claims.

We claim:

1. An immunogenic composition, comprising: a varicella zoster virus (VZV) glycoprotein E (gE) antigen and a toll-like receptor 9 (TLR9) agonist, wherein the TLR9 agonist is an oligonucleotide of from 10 to 35 nucleotides in length comprising an unmethylated cytidine-phospho-guanosine (CpG) motif, wherein the oligonucleotide comprises the sequence of 5'-TGACTGTGAA CGTTCGAGAT GA-3' (SEQ ID NO:1), wherein the immunogenic composition comprises from about 3000 μg to about 6000 μg of the oligonucleotide and from about 50 μg to about 100 μg of the gE antigen.

2. The immunogenic composition of claim 1, wherein the oligonucleotide comprises a modified nucleoside selected from the group consisting of 2'-deoxy-7-deazaguanosine, 2'-deoxy-6-thioguanosine, arabinoguanosine, 2'-deoxy-2' substituted-arabinoguanosine, and 2'-O-substituted-arab-inoguanosine.

3. The immunogenic composition of claim 1, wherein the oligonucleotide comprises at least one phosphorothioate linkage, or wherein all nucleotide linkages are phosphorothioate linkages.

4. The immunogenic composition of claim 3, wherein the oligonucleotide is a single-stranded oligodeoxynucleotide.

5. The immunogenic composition of claim 1, wherein the VZV gE antigen is a truncated, recombinant protein devoid of signal peptide, transmembrane and cytoplasmic domains of a full-length VZV gE antigen.

6. The immunogenic composition of claim 1, further comprising an aluminum salt adjuvant.

7. The immunogenic composition of claim 6, wherein the aluminum salt adjuvant comprises one or more of the group consisting of amorphous aluminum hydroxyphosphate sulfate, aluminum hydroxide, aluminum phosphate, and potassium aluminum sulfate.

8. The immunogenic composition of claim 6, wherein the aluminum salt adjuvant comprises aluminum hydroxide.

9. A kit comprising:

i) an immunogenic composition comprising a varicella zoster virus (VZV) glycoprotein E (gE) antigen and a toll-like receptor 9 (TLR9) agonist, wherein the TLR9 agonist is an oligonucleotide of from 10 to 35 nucleotides in length comprising an unmethylated cytidine-phospho-guanosine (CpG) motif, wherein the oligonucleotide comprises the sequence of 5'-TGACTGTGAA CGTTCGAGAT GA-3' (SEQ ID NO:1), wherein the immunogenic composition comprises from about 3000 μg to about 6000 μg of the oligonucleotide and from about 50 μg to about 100 μg of the gE antigen, and ii) instructions for administration of the immunogenic composition to stimulate an immune response against the gE antigen in a mammalian subject.

10. A method for stimulating an immune response against varicella zoster virus (VZV) in a mammalian subject, comprising administering to a subject in need an immunogenic composition comprising a varicella zoster virus (VZV) glycoprotein E (gE) antigen and a toll-like receptor 9 (TLR9) agonist, wherein the TLR9 agonist is an oligonucleotide of from 10 to 35 nucleotides in length comprising an unmethylated cytidine-phospho-guanosine (CpG) motif, and wherein the oligonucleotide comprises the sequence of 5'-TGACTGTGAA CGTTCGAGAT GA-3' (SEQ ID NO: 1), wherein the immunogenic composition comprises from about 3000 μg to about 6000 μg of the oligonucleotide and from about 50 μg to about 100 μg of the gE antigen to a mammalian subject.

11. The method of claim 10, wherein the immunogenic composition is administered by intramuscular injection.

12. The method of claim 10, wherein the immunogenic composition further comprises an aluminum salt adjuvant.

13. The immunogenic composition of claim 1, wherein the immunogenic composition comprises about 6000 μg of the oligonucleotide.

14. The immunogenic composition of claim 1, wherein the immunogenic composition comprises about 100 μg of the gE antigen.

15. The immunogenic composition of claim 1, wherein the immunogenic composition comprises about 6000 μg of the oligonucleotide and 100 μg of the gE antigen.

16. An immunogenic composition, comprising: a varicella zoster virus (VZV) glycoprotein E (gE) antigen and a toll-like receptor 9 (TLR9) agonist, wherein the TLR9 agonist is an oligonucleotide comprising the sequence of 5'-TGACTGTGAA CGTTCGAGAT GA-3' (SEQ ID NO:1), and an aluminum salt adjuvant, wherein the immunogenic composition comprises about 6000 µg of the oligonucleotide and about 100 µg of the gE antigen.

17. The method of claim 10, wherein the VZV gE antigen is a truncated, recombinant protein devoid of signal peptide, transmembrane and cytoplasmic domains of a full-length VZV gE antigen.

18. The method of claim 10, wherein the immunogenic composition comprises about 6000 µg of the oligonucleotide.

19. The method of claim 10, wherein the immunogenic composition comprises about 100 µg of the gE antigen.

20. The method of claim 10, wherein the immunogenic composition comprises about 6000 µg of the oligonucleotide and 100 µg of the gE antigen.

21. The method of claim 20, wherein the immunogenic composition further comprises an aluminum salt adjuvant.

22. The immunogenic composition of claim 16, wherein the VZV gE antigen is a truncated, recombinant protein devoid of signal peptide, transmembrane and cytoplasmic domains of a full-length VZV gE antigen.

23. A method for stimulating an immune response against varicella zoster virus (VZV) in a mammalian subject, comprising administering to a subject in need the immunogenic composition of claim 16.

24. The method of claim 23, wherein the immunogenic composition is administered by intramuscular injection.

\* \* \* \* \*